United States Patent
Lam et al.

(10) Patent No.: US 8,436,121 B2
(45) Date of Patent: May 7, 2013

(54) TWO-COMPONENT SEALANT COMPRISING CROSS-LINKED POLYALKYLENE OXIDE

(75) Inventors: Peter Kwok Hing Lam, Frederiksberg C (DK); Henrik Edvardsen, Copenhagen N (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/427,570

(22) Filed: Mar. 22, 2012

(65) Prior Publication Data

US 2012/0180699 A1    Jul. 19, 2012

Related U.S. Application Data

(62) Division of application No. 12/310,395, filed as application No. PCT/DK2007/050124 on Sep. 6, 2007.

(30) Foreign Application Priority Data

Sep. 8, 2006    (DK) .................................. 2006 01157

(51) Int. Cl.
*C08G 77/12*    (2006.01)
(52) U.S. Cl.
USPC .............................................. 528/31; 528/25

(58) Field of Classification Search .................... 528/31, 528/25
See application file for complete search history.

(56) References Cited

U.S. PATENT DOCUMENTS

2008/0311396 A1 * 12/2008 Hamada et al. ......... 428/355 EN

FOREIGN PATENT DOCUMENTS

WO    2005 032401    *    4/2005

* cited by examiner

*Primary Examiner* — Kuo-Liang Peng
(74) *Attorney, Agent, or Firm* — Coloplast Corp., Coloplast A/S

(57) ABSTRACT

The present invention relates to a two-component sealant comprising a first part and a second part wherein
   a) the first part (X) comprises:
      (i) a polyalkyleneoxide polymer having one or more unsaturated end groups
      (ii) an addition reaction catalyst
   b) the second part (Y) comprises:
      (i) an organosiloxane comprising one or more Si—H groups.

The present invention also relates to medical devices used in connection with the sealant, mixing devices for delivering and mixing the first part and the second part of the sealant, and methods for applying the sealant.

13 Claims, No Drawings

TWO-COMPONENT SEALANT COMPRISING CROSS-LINKED POLYALKYLENE OXIDE

This is a divisional of application Ser. No. 12/310,395, filed Feb. 24, 2009, which was a national stage of PCT/DK2007/050124 filed Sep. 6, 2007 and published in English, which claims priority from Danish Application No. PA 2006 01157 filed Sep. 8, 2006, each of which is hereby incorporated by reference in its entirety.

FIELD OF THE INVENTION

The present invention relates to a novel two-component sealant which crosslinks in-situ comprising cross-linked polyalkylene oxide.

The present invention also relates to medical devices used in connection with the sealant, mixing devices for delivering and mixing the first part and the second part of the sealant, and methods for applying the sealant.

BACKGROUND OF THE INVENTION

Surgical procedures, known as ostomies, are some times necessitated due to inflammatory bowel disease, cancer, or injury. An ostomy creates an artificial opening (stoma) in the abdomen for the elimination of bodily waste. Since the ostomy patients are unable to control the passage of bodily waste material, use is made of an appliance attached to the body to collect this material. Conventional available ostomy appliances consist of a pouch, made up of a barrier plastic material, attached to a hydrocolloid containing synthetic rubber based adhesive gasket capable of adhering to the skin around the stoma. The adhesive gasket is capable of anchoring the appliance to the skin for time periods ranging from a few hours to as long as 10 days. The adhesive gasket does protect the peristomal skin. However, it is very difficult for the ostomate to cut a hole in the wafer to fit perfectly around the stoma to achieve a fluid proof seal between the stomal opening of the gasket and the stoma. Even for pre-cut adhesive gaskets it can be difficult to obtain at perfect fit around the stoma, to achieve a fluid proof seal between the stomal opening of the gasket and the stoma. Therefore, some areas of the peristomal skin may remain exposed and become vulnerable to the deleterious effects of the intestinal effluents, which can cause serious irritation, excoriation, and eventual breakdown of the skin contiguous to the stoma. In addition, the fluid leakage may also cause disintegration of the gasket, resulting in breach of its barrier properties and exacerbating the problem of skin protection. Another frequent cause of peristomal skin complications is stomal effluent undermining a skin barrier due to irregularities in stoma placement, stoma shape, retraction or scarring. When peristomal surface unevenness is severe, the appliance gasket may fail to achieve an acceptable seal resulting in undermining of the gasket by the stomal effluent, causing leakage, discomfort and pain. For these reasons, many ostomates use one of the additional means available in the form of pastes, hydrocolloid powders, karaya seal rings, skin barrier rings, or adhesive strips to augment the sealing function of the gasket. One of the disadvantages of such pastes is that some of them contain solvents, which are irritating to skin. Another disadvantage is that the pastes are easily subject to disintegration by absorption of effluent or moisture. Pastes are generally not very cohesive, and therefore often leave residues upon removal. Body movements could also disrupt the sealing properties. Thorough cleaning is required in order that a new plaster may stick well to the application area. This procedure may further irritate the skin.

U.S. Pat. No. 4,204,540 describes a composition adapted for use around the stoma and consisting of a homogeneous mixture of a pressure-sensitive adhesive component, mineral oil, and hydrocolloid gums or cohesive strengthening agents or a mixture of hydrocolloid gums and cohesive strengthening agents. A balance of different components in the mixture provides compositions which can be shaped by hand to seal the skin surface between the gasket and the stoma.

U.S. Pat. No. 4,231,369 describes a gel-like sealant composition composed of a physical mixture of tackified styrene-olefin-styrene block copolymer having at least one hydrocolloid dispersed therein.

U.S. Pat. No. 4,350,785 describes an ostomy paste formulated as mixtures of water absorbing particulate hydrocolloid gums and organic solvent (e.g. alcohol) solutions of adhesive film forming resins, such as poly(methyl vinyl ether/maleic acid), having increased resistance to urine and intestinal fluids by incorporating a small amount of colloidal silica, preferably fumed silica.

U.S. Pat. No. 4,578,065 describes protective sealing compositions in the form of molded rings or sheets, which comprise gelled mixtures of water absorbing particulate hydrocolloid gum and non-toxic polyhydroxyalcohol, having increased resistance to the drained fluid (e.g. urine or intestinal fluids) by incorporating a small amount of fumed silica or colloidal silica gel.

U.S. Pat. No. 4,477,325 to Osburn describes sealant or paste composition of hydrocolloids in a network of an elastomeric copolymer of ethylene and vinyl acetate, and polyisobutylene; the mechanical strength and fluid endurance of which is enhanced by crosslinking, produced by irradiating the mixture.

U.S. Pat. No. 4,738,257 to Meyer et al describes a continuous elastomeric phase, formed by cross-linking to form a network, and distinguishes itself by stating that in Sorensen and Osburn, above, that after absorbing enough water, the hydrocolloid loses its wet tack, or ability to adhere to the skin to form a sealant or shield.

U.S. Pat. No. 5,496,296 describes an ostomy appliance having an adhesive gasket, which includes a flexible patch which may be formed of non-woven material and is covered on one side with a first layer of moisture absorbing pressure-sensitive adhesive material surrounding the stomal opening, and a second layer of a soft, easily deformable, extrudable fluid resistant gasket that prevents stomal fluids form contacting the peristomal skin surfaces and the first layer of the adhesive and possibly dissolving that layer and/or disrupting its attachment to skin.

WO 2006/075949 describes a pre-formed, very soft sealant ring. It is pre-formed, and so can be limited as to how well it can adapt to a variety of skin sites of different shapes or sizes. The preferred material is described to be silicone rubber, which has adhesion problems to most materials, including SIS and PIB, the common material used for ostomy adhesive plates.

The best fitting sealant achievable would come from a flowable or pliable system which wets out easily into the contours and crevices of the skin and adapts to the surface of the skin. There should also be an increase in cohesion after application for it to function safely and to be easy removable after use.

U.S. Pat. No. 6,068,852 describes a 2 part, polymerizable, skin sealant or shield which cures in-situ at the skin site. It describes the use of acrylic copolymers and monomers which are crosslinked by the use of free radical polymerization initiator.

Acrylic monomers and free radical initiators are known to be toxic to skin. The initiator can also be inhibited by the application environment, such as oxygen, moisture and pH, so that crosslinking can not be achieved effectively. Furthermore, the above mentioned systems use relatively low to very low moisture permeable polymers which are not inducive to transporting moisture away from the skin, giving potential maceration problems.

One solution is to increase the amount of water absorbent material, which has the effect of swelling or weakening the polymer matrix. This in turn reduces the sealing or adhesion properties and the erosion resistance of the seal, leading to reduced wear time and leakage problems.

WO04108175 discloses a 2 component silicone composition for application to the skin.

JP2004067720 discloses a crosslinked polyoxyalkylene based polymer matrix which is pre-reacted at 90° C. on a fabric carrier. Both reaction components for the crosslinked polymer are silicone oligomers or copolymers.

Silicone systems, due to the nature of their surface properties, have adhesion problems with most commonly used adhesives in the medical applications of interest except with silicone based devices. This severely limits the usability of silicone compositions. Furthermore, silicones in general do not have very high water transport properties, thus may lead to maceration problems.

WO 2005/032401 describes a PSA sheet based on PPO polymers having low irritation to the skin and high moisture permeability. It is a pre-formed adhesive crosslinked at over 100° C.

It has now been surprisingly found that liquid PPO polymers can be crosslinked at workable rates at body temperatures on the skin site to provide a very good fit around the contours of the skin site, thereby providing very good sealing or barrier properties against leakage around the stoma. It is soft and comfortable to wear, easy to remove in one piece, skin friendly, and does not cause adhesion problems when later using other types of adhesives.

Furthermore, it provides superior moisture permeability, excellent erosion resistance, again improving safety against leakage, fast curing of between 5 to 30 min. under application conditions.

SUMMARY OF THE INVENTION

Accordingly, the present invention relates to a two-component sealant comprising a first part and a second part wherein
a) the first part (X) comprises:
  (i) a polyalkyleneoxide polymer having one or more unsaturated end groups
  (ii) an addition reaction catalyst
b) the second part (Y) comprises:
  (i) an organosiloxane comprising one or more Si—H groups.

The present invention also relates to medical devices used in connection with the sealant, mixing devices for delivering and mixing the first part and the second part of the sealant, and methods for applying the sealant.

DETAILED DESCRIPTION OF THE INVENTION

The present invention provides a two-component sealant as described above which can be crosslinked at workable rates at body temperatures on the skin site to provide a very good fit around the contours of the skin site, thereby providing very good sealing or barrier properties against leakage around stoma. It is soft and comfortable to wear, but easy to remove in one piece, skin friendly, and does not cause adhesion problems with replacement adhesives.

According to one embodiment of the invention, the first part (X) comprises:
  (i) a polyalkyleneoxide polymer having one or more unsaturated end groups, and wherein more than 90% w/w of the polyalkylene oxide polymer consist of polymerised alkyleneoxide moities having three or more carbon atoms, and
  (ii) an addition reaction catalyst
b) the second part (Y) comprises:
  (i) an organosiloxane comprising one or more Si—H groups.

According to another embodiment of the invention, the first part (X) comprises:
  (i) a polyalkyleneoxide polymer having at least two unsaturated end groups, and wherein more than 90% w/w of the polyalkylene oxide polymer consist of polymerised alkyleneoxide moities having three or more carbon atoms, and
  (ii) an addition reaction catalyst
b) the second part (Y) comprises:
  (i) a polysiloxane cross-linking agent comprising 3 or more Si—H groups and optionally
  (ii) a polysiloxane chain extender comprising up to 2 Si—H groups.

According to a preferred embodiment of the invention the second part comprising a polyalkyleneoxide polymer of the type that is defined to be used in the first part.

According to a preferred embodiment of the invention the first part comprises the polyalkyleneoxide polymer in amounts of 80-98% w/w and the addition reaction catalyst in amounts of 0.01-1% w/w and the second part comprises the polyalkyleneoxide polymer in amounts of 0 to 98, preferably 80-98% w/w and the siloxane in amounts of 1-100, preferably 1-10% w/w.

The sealant of the invention may comprise the above mentioned ingredients, as well as other ingredients, such as other polymers or polymeric product.

The polyalkylene oxide polymer having one or more unsaturated groups may be branched or linear.

However, suitably, the polyalkylene oxide polymer is linear and has two unsaturated end groups.

In one particular embodiment of the invention the polyalkylene oxide polymer is polypropyleneoxide.

The polypropylene oxide having unsaturated end groups may be a compound of formula

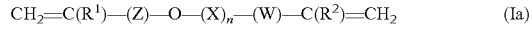

$$CH_2=C(R^1)-(Z)-O-(X)_n-(W)-C(R^2)=CH_2 \quad \text{(Ia)}$$

or

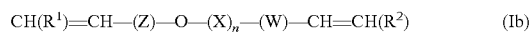

$$CH(R^1)=CH-(Z)-O-(X)_n-(W)-CH=CH(R^2) \quad \text{(Ib)}$$

wherein
$R^1$ and $R^2$ are independently selected from hydrogen and $C_{1-6}$-alkyl;
Z and W is $C_{1-4}$-alkylene;
X is —$(CH_2)_3$—O— or —$CH_2$—$CH(CH_3)$—O—; and
n is 1-900, more preferred 10-600, or most preferred 20-600.

The number average molecular weight of the polyalkylene oxide having unsaturated end groups is suitably between 500 and 100000, more preferred between 500 and 50,000 and most preferred between 1000 and 35,000.

Polypropylene oxide having unsaturated end groups may be prepared as described in U.S. Pat. No. 6,248,915 and WO 05/032401 or analogously to the methods described therein. Other polyalkylene oxide polymers may be prepared analogously.

The polysiloxane cross-linking agent comprising 3 or more Si—H groups is suitable a compound having the formula

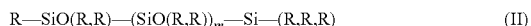

$$R\text{—}SiO(R,R)\text{—}(SiO(R,R))_m\text{—}Si\text{—}(R,R,R) \quad (II)$$

wherein
at least three of the groups R is hydrogen and the rest of the groups R are each independently selected from $C_{1-12}$-alkyl, $C_{3-8}$-cycloalkyl, $C_{6-14}$-aryl, and $C_{7-12}$-arylalkyl; and
m is 5-50, or preferably 10-40. The number average molecular weight as determined by GPC is suitably 500-3000.

One or more cross-linking agents of formula (II) may be used in the second part of the two-component sealant.

In one embodiment of the invention, a mixture of one or more cross-linking agents of formula (II) comprising 3 or more Si—H groups and a polysiloxane chain extender comprising up to 2 Si—H groups is used in the cross-linking reaction.

The polysiloxane chain extender is suitably a compound having the formula

$$R^3\text{—}SiO(R^3,R^3)\text{—}(SiO(R^3,R^3))_m\text{—}Si\text{—}(R^3,R^3,R^3) \quad (III)$$

wherein
up to 2 of the groups $R^3$ is hydrogen and the rest of the groups $R^3$ are each independently selected from $C_{1-12}$-alkyl, $C_{3-8}$-cycloalkyl, $C_{6-14}$-aryl, and $C_{7-12}$-arylalkyl; and
m is 0-50. The number average molecular weight as determined by GPC is suitably between 200 and 65000, most preferably between 200 and 17500.

As used herein $C_{1-12}$-alkyl means a linear or branched alkyl group having 1 to 12 carbon atoms, $C_{1-8}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the —$(SiO(R^3,R^3))_m$— chain of the compound of formula (II).

The polysiloxane cross-linking agent and the chain extender may be prepared as described in Japanese Patent Application 2002-224706 and WO 05/032401 or analogously to the methods described therein.

An addition reaction is, in its simplest terms, a chemical reaction in which the atoms of an element or compound react with a double bond or triple bond in an organic compound by opening up one of the bonds and becoming attached to it, forming one larger compound.

Addition reactions are limited to chemical compounds that have multiple-bonded atoms.

Hydrosilylation is an addition reaction between, for example, a carbon-carbon double bond in a compound and a reactive hydrogen from a hydrogen siloxane.

Suitable addition reaction catalysts are any hydrosilylation catalysts, preferably platinum (Pt) catalysts. Pt-catalysts for the first part of the two-component sealant are described in U.S. Pat. No. 6,248,915. In consideration of toxicity potential, Pt complex catalyst where Pt is at a valency state of zero is preferred. Preferred catalysts are platinum-vinylsiloxan and platinum-olefin complexes, such as Pt-divinyl tetramethyl disiloxane.

The two components are mixed immediately before delivery. A wide range of devices for delivering and mixing the two components can be used.

The mixing and reaction is suitably carried out at room to body temperature between 25° C. and 40° C. It is not necessary to use a solvent for the reaction, which is an advantage, but especially in the preparation of sealants for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 1.0.

The amount of polysiloxane used for the cross-linking is suitably less than 15% w/w, and more preferred below 10% w/w of the amount of polyalkylene oxide polymer having unsaturated end groups.

The cross-linking reaction does not lead to complete cross-linking of all the polyalkylene oxide polymers. The sealant comprises a mixture of cross-linked and non cross-linked polyalkylene oxide polymer.

Good moisture handling is important for skin applications. Management of moisture from skin can be by permeation or absorption or both methods through the sealant.

In some applications high permeability without water absorption is preferred as this transports the moisture away from the skin surface, without sacrificing other properties such as erosion resistance and swelling resistance.

The addition of hydrocolloid or other organic or inorganic moisture absorbing particles or polymers is also feasible to improve the moisture handling properties. The type and amount added will influence other parameters such as mechanical and erosion properties and water vapor transmission.

According to a preferred embodiment of the invention one or both of the first part and the second part comprising one or more hydrocolloids in amounts of 5-35% w/w.

According to another preferred embodiment of the invention one or both of the first part and the second part do not comprise hydrocolloids.

Optionally, non absorbent particles or polymers, such as potatoe starch, may be added to the composition. These fillers do not affect the moisture absorption characteristics significantly. They are especially useful in reducing the concentrations of active ingredients, lowering toxicity potential and costs. Further these fillers may also effect the mechanical properties of the final system in regards to hardness and adhesion.

According to a preferred embodiment of the invention one or both of the first part and the second part comprising a filler and/or a stabilizer in the amounts of 0, 5-65% w/w with the polymer in the amounts from 35-98% w/w.

Another optional ingredient is a rheological modifier, such as thixotropic or anti-settling agents. These help to control and modify the viscosity to suit the application method, and prevent the sedimentation of other particulate ingredients. Examples include fumed or colloidal silica, e.g. Aerosil 202 from Degussa.

According to a preferred embodiment of the invention one or both of the first part and the second part comprising a rheological modifier in amounts of 0, 1-10% w/w.

Oils, tackifiers, plasticisers may be also added to modify properties.

Other optional functional ingredients include colouring agents, organic or inorganic pigments, such as iron oxide, to give a distinctive colour to one or both components for easy identification and help with following the mixing. Other ingredients may include antioxidants, pH buffers. Furthermore ingredients such as aloe vera or other functional ingredients eg. skinfriendliness can be added to one or both components of the composition.

According to a preferred embodiment of the invention one or both of the first part and the second part comprise one or more functional additives.

The composition of the invention is compatible with and can adhere to a wide variety of adhesives with which it is intended to cooperate, and can therefore be removed with a typical adhesive used with a standard medical device in one piece without leaving residue, or oil, which make replacement adhesives difficult to stick. Examples of such adhesives include PPO adhesives described in WO 2005/032401, and hot-melt adhesives as described in U.S. Pat. No. 5,559,165.

Another embodiment of the invention is that the invention composition can be easily separated from the adhesive plate of the medical device, while still attached to the skin, when the device is removed, so that it can be removed in one piece separately.

The invention also relates to medical devices comprising a sealant as described above. The invention is especially suitable to be used in conjunction with medical devices for ostomy applications.

The present invention can be mixed by a number of well known methods typical for mixing 2 component systems and applied directly onto the skin area, followed by the application of the ostomy device with an adhesive plate for attachment to the skin.

Alternatively, the mixed sealant can be applied around the central opening of the adhesive plate of the ostomy device, and the device is placed at the stoma as normal.

According to a preferred embodiment of the invention a method for making a custom made, skin friendly, protective, aqueous fluid managing skin seal or shield using a two-component sealant according to the invention, comprises the steps,
(i) mixing parts one and two to form a paste,
(ii) applying the paste to the area of the skin where a seal or shield is desired, in sufficient quantity to allow the paste to flow into the contours, folds, and crevices of the skin, and therein undergo self curing to form a soft, flexible and coherent rubbery mass, tightly adhering to the skin.

According to another preferred embodiment of the invention a method for making a custom made, skin friendly, protective, aqueous fluid managing skin seal or shield using a two-component sealant according to the invention, comprises the steps,
(i) mixing parts one and two to form a paste,
(ii) applying the appliance or device to the skin site,
(iii) then applying the paste into or onto the visible crevice or skin site, where after the paste undergoes self curing to form a soft, flexible and coherent rubbery mass, tightly adhering to the skin.

According to yet another preferred embodiment of the invention a method for making a custom made, skin friendly, protective, aqueous fluid managing skin seal or shield using a two-component sealant according to the invention, comprises the steps,
(i) mixing parts one and two to form a paste,
(ii) applying to an appliance or device to be attached to the skin, a sufficient quantity of the paste to allow the paste to flow into the contours, folds, and crevices of the skin when applied, and,
(iii) applying the apparatus or device to the skin within a short period of time, 1-30 minutes preferably 5-15 minutes, of mixing parts one and two, whereafter the paste undergoes self curing to form a soft, flexible and coherent rubbery mass, tightly adhering to the skin.

The invention may also have other skin protecting applications, such as use with devices for the management of fecal incontinence and for use around fluid drainage openings like wound or surgical incision sites.

The sealant according to the invention may also be used to create a protective barrier to prevent skin damage.

The present invention could also be used for any applications where the skin will benefit from a soft, comfortable, moisture handling protective layer, e.g. masks.

One embodiment of the invention relates to a delivery device for the two-component sealant according to the invention wherein said delivery device dispensing said sealant in the necessary ratios of the first part to the second part to form the desired sealant.

A wide range of devices for delivering and mixing the first part and the second part are known. The choice of device for delivering the first part and the second part of the sealant can influence ease of use, handling, viscosity, mixing, curing, and cost. An example of a mixing and delivery device can be a 2-chamber syringe fitted with a static mixer. Other devices could be a 2 chamber bag for 1 or more times use. The device could also be as simple as 2 vials or more containing the first part and the second part, from were the two parts are poured and mixed by hand. The device could be powered by hand or e.g. by air/gas pressure. The sealant could be applied as a foam or a thin film by means of aerosol.

Experimental

The following materials were used in the experimental part:

HPM-502=methyl hydrosiloxane-phenyl methyl siloxane copolymer, hydride terminated, 75-110cs, from ABCR AA2000=Polypropylenglykol 2000, allyl-terminated polyether (poly propylene oxide), from Clariant Catalyst Pt-VTS. Pt-VTS is Pt-divinyl tetramethyl disiloxane in IPA (Pt 3.0 wt %).

Aerosil® R202, fumed silica anti-settling agent from Degussa

ACX003, allyl-terminated polyether (poly propylene oxide) viscosity 16 Pa·s from Kaneka.

CR500, poly-alkyl hydrogen siloxane curing agent available from Kaneka.

Silicone A: Dow Corning 9800 Part A
Silicone B: Dow Corning 9800 Part B
PU film: BL9601, Intellicoat. MVTR=10000 g/m$^2$/24 h
Bayferrox 960, iron oxide powder from Lanxess
Aquasorb A500, sodium carboxymethyl cellulose, Aqualon Examples for Component A Put the ingredients, PPG AA2000, Pt-VTS at the correct weights in a container. Stir to mix using a wooden spatula. If fillers are added, then add filler in small increments and mix. Finally adjust viscosity with Aerosil® R202 by adding in small increments and mixing until a smooth mixture is obtained without any grittiness or lumps.

Examples for Component B

Put the ingredients, PPG AA2000, HPM-502 at the correct weights in a container. Stir to mix using a wooden spatula. If fillers are added, then add filler in small increments and mix. Finally adjust viscosity with Aerosil® R202 by adding in small increments and mixing until a smooth mixture is obtained without any grittiness or lumps.

Examples of Mixing Sealants

Add 1 part component A (containing catalyst) to 1 part component B (containing Silicone crosslinker). Mix thoroughly using a wooden spatula for 2-5 min.

Gelation is visually determined when the mixture is no longer fluid or paste-like.
Compositions

| Component | A1 | B1 | B2 | A2 | B3 | A3 | B4 | B5 | A4 | B6 |
|---|---|---|---|---|---|---|---|---|---|---|
| PPG AA2000 | 48.55 | 44.64 | 44.26 | 48.44 | 91.77 | 99.60 | 80.12 | 93.68 | | |
| HPM-502 | | 4.00 | 4.38 | | 8.23 | | 19.88 | 6.32 | | |
| ACX003 | | | | | | | | | 49.16 | 45.72 |
| CR500 | | | | | | | | | | 3.67 |
| Pt-VTS | 0.09 | | | 0.19 | | 0.40 | | | 0.24 | |
| Aquasorb A500 | | | | | | | | | 20.00 | 20.00 |
| Potatoe starch | 48.64 | 48.64 | 48.64 | 48.64 | | | | | 29.40 | 29.40 |
| Aerosil ® R202 | 2.72 | 2.72 | 2.72 | 2.72 | | | | | 1.20 | 1.20 |
| Bayferrox 960 | | | | | | | | | | 0.01 |

Ingredients in w/w %

Sealant Compositions and Results

| A1 + B1 | not gelled |
|---|---|
| A2 + B1 | gelled within 20 min RT |
| A2 + B2 | gelled within 20 min RT |

The above results show examples where fillers and additives are used. The catalyst must be above a certain level to achieve good reaction at room temperature. But catalyst is also very expensive, and so it is kept at the lowest level to achieve good reaction at room temperature (RT) for it to be useful commercially.

| A3 + B3 | gelled within 20 min RT |
|---|---|
| A3 + B4 | gelled within 5 min RT |
| A3 + B5 | not gelled |

The above results show sealant compositions without fillers. The crosslinker level must be sufficiently high in order to achieve a gel of the required cohesion for good sealant properties, and to achieve gelation in practical times, typical 5-30 min.
Methods Determination of moisture vapour transmission rate (MVTR)

MVTR is measured in grams per square meter ($g/m^2$) over a 24 hours period using an inverted cup method.

A container or cup that is water and water vapour impermeable having an opening is used. 20 ml saline water (0.9% NaCl in demineralised water) is placed in the container and the opening is sealed with the test film. The container, with a duplicate, is placed into an electrically heated humidity cabinet and the container or cup is placed up side down such that the water is in contact with the adhesive. The cabinet is maintained at 37° C. and 15% relative humidity (RH). After about an hour, the containers are considered to be in equilibrium with the surroundings and it is weighed. 24 h after the first weighing, the containers are weighed again. The difference in weight is due to evaporation of vapour transmitted through the test film. This difference is used to calculate Moisture vapour transmission rate or MVTR. MVTR is calculated as the weight loss after 24 h divided by the area of the opening in the cup ($g/m^2/24$ h). An error is introduced by using a supporting PU film. However, the water permeability of the used film is very high (10000 $g/m^2/24$ h) and the error that is introduced is therefore very small.

Example of Sealant Prepared by A4 and B6

A sealant of the invention was prepared by mixing 1 part of A4 and 1 part of B6. The components were mixed thoroughly using a wooden spatula for 2-5 min. To produce the sheet stock, the mixture was coated on a silicone coated release liner. Coating thickness was 1000 µm. The samples are cured at room temperature for 20 min.

Comparative Example C1

First, 4 parts of Silicone A and 4 parts of Silicone B were weighed and mixed thoroughly with a spetula and after that, 2 parts Aquasorb was added.

After mixing for approx. 5 min., the mixture was formed into a sheet stock material having a thickness of approximately 0.3 mm by coating a layer onto a 30 µm PU film (Inspire 2301 from Intelicoat). The samples were cured at 100° C. for 1 hr in order to ensure complete reaction. Then it was cooled to ambient temperature ready for use. The resultant flat plate was cut into the desired shapes.
MVTR Results

| Composition | Thickness/mm | MVTR/$g/m^2/24$ hr |
|---|---|---|
| A4 + B6 | 1.00 | 600 |
| C1 | 0.30 | 378 |

As can be seen, the invention at higher thickness than a comparison example of silicone gel still gives significantly higher permeability. Hence the invention sealant is desirably more permeable than, for example, a similar system based on silicone, making the current invention highly preferable for the intended applications.

The invention claimed is:

1. A method for making a custom made, skin friendly, protective, aqueous fluid managing skin seal or shield using a two-component sealant including a first part (X) and a second part (Y), wherein
   a) the first part (X) comprises:
      (i) a polyalkyleneoxide polymer having one or more unsaturated end groups; and
      (ii) an addition reaction catalyst; and
   b) the second part (Y) comprises:
      (i) an organosiloxane comprising one or more Si-H groups the method, comprising the steps of,
   (i) mixing parts one and two to form a paste,
   (ii) applying the paste to the area of the skin where a seal or shield is desired, in sufficient quantity to allow the paste to flow into the contours, folds, and crevices of the skin, and therein undergo self curing to form a soft, flexible and coherent rubbery mass, tightly adhering to the skin.

2. The method according to claim 1, wherein in the two-component sealant:
   a) the first part (X) comprises:
      (i) a polyalkyleneoxide polymer having one or more unsaturated end groups, and wherein more than 90% w/w of the polyalkylene oxide polymer consists of polymerized alkyleneoxide moieties having three or more carbon atoms, and
      (ii) an addition reaction catalyst, and
   b) the second part (Y) comprises:
      (i) an organosiloxane comprising one or more Si-H groups.

3. The method according to claim 1, wherein the polyalkyleneoxide polymer of the first part (X) has at least two unsaturated end groups, and wherein more than 90% w/w of the polyalkylene oxide polymer of the first part (X) consists of polymerized alkyleneoxide moieties have three or more carbon atoms, and wherein the polysiloxane cross-linking agent of the second part (Y) has 3 or more Si-H groups, and optionally a polysiloxane chain extender having up to 2 Si-H groups.

4. The method according to claim 1 wherein the second part (Y) comprises a second polyalkyleneoxide polymer having one or more unsaturated end groups.

5. The method according to claim 1, wherein the addition reaction catalyst is a Pt vinyl siloxane complex.

6. The method according to claim 1, wherein the first part (X) comprises the polyalkyleneoxide polymer in amounts of 80-98% w/w and the addition reaction catalyst in amounts of 0.01-1% w/w, and the second part comprises the polyalkyleneoxide polymer in amounts of 0 to 98% and the siloxane in amounts of 1-100% w/w.

7. The method according to claim 1, wherein the second part comprises the polyalkyleneoxide polymer in amounts of 80-98% and the siloxane in amounts of 1-10% w/w.

8. The method according to claim 1, wherein one or both of the first part (X) and the second part (Y) includes a filler and/or a stabilizer in an amounts of 0.5-65% w/w with the polymer in the amount of from 35-98% w/w.

9. The method according to claim 1, wherein one or both of the first part (X) and the second part (Y) includes a rheological modifier in an amount of 0.1-10% w/w.

10. The method according to claim 1, wherein one or both of the first part (X) and the second part (Y) includes one or more hydrocolloids in amounts of 5-35% w/w.

11. The method according to claim 1, wherein one or both of the first part (X) and the second part (Y) do not include hydrocolloids.

12. The method according to claim 1, wherein one or both of the first part (X) and the second part (Y) includes one or more functional additives.

13. The method according to claim 1, wherein the polyalkylene oxide polymer is polypropyleneoxide.

* * * * *